United States Patent
Foster et al.

(10) Patent No.: US 8,812,134 B2
(45) Date of Patent: Aug. 19, 2014

(54) HELIX FIXATION MECHANISM

(75) Inventors: Arthur J. Foster, Centerville, MN (US); Matthew J. Miller, Stillwater, MN (US)

(73) Assignee: Cardiac Pacemakers Inc., St. Paul, MN (US)

( * ) Notice: Subject to any disclaimer, the term of this patent is extended or adjusted under 35 U.S.C. 154(b) by 948 days.

(21) Appl. No.: 12/882,778

(22) Filed: Sep. 15, 2010

(65) Prior Publication Data
US 2011/0112619 A1    May 12, 2011

Related U.S. Application Data

(60) Provisional application No. 61/260,583, filed on Nov. 12, 2009.

(51) Int. Cl.
*A61N 1/05*    (2006.01)

(52) U.S. Cl.
CPC ....... *A61N 1/0575* (2013.01); *A61N 2001/0578* (2013.01)
USPC ........................................................ 607/127

(58) Field of Classification Search
CPC ....... A61N 1/05; A61N 1/056; A61N 1/0565; A61N 1/057; A61N 1/0573; A61N 1/0575; A61N 1/059
USPC .................. 607/120, 126–127, 131
See application file for complete search history.

(56) References Cited

U.S. PATENT DOCUMENTS

| | | | |
|---|---|---|---|
| 4,886,074 A | 12/1989 | Bisping | |
| 5,522,876 A * | 6/1996 | Rusink | 607/127 |
| 5,776,178 A | 7/1998 | Pohndorf et al. | |
| 5,871,531 A * | 2/1999 | Struble | 607/126 |
| 6,078,840 A * | 6/2000 | Stokes | 607/127 |
| 6,501,994 B1 | 12/2002 | Janke et al. | |
| 6,687,550 B1 | 2/2004 | Doan | |
| 7,162,310 B2 | 1/2007 | Doan | |
| 7,197,362 B2 * | 3/2007 | Westlund | 607/127 |
| 7,212,879 B2 | 5/2007 | Hagino | |
| 7,218,870 B2 | 5/2007 | Hirobe | |
| 2003/0060868 A1 | 3/2003 | Janke et al. | |
| 2008/0234792 A1 | 9/2008 | Reddy et al. | |

FOREIGN PATENT DOCUMENTS

WO    WO 2009/070074 A1 *    6/2009    ............... A61N 1/05

* cited by examiner

*Primary Examiner* — Carl H Layno
*Assistant Examiner* — Jessica Anthony
(74) *Attorney, Agent, or Firm* — Faegre Baker Daniels LLP

(57) ABSTRACT

An implantable lead may have a distal assembly including a coupler and a fixation helix secured to the coupler. The fixation helix may be formed of a filar having a non-circular cross-sectional profile having a major dimension and a minor dimension. The major dimension may be disposed transversely to a longitudinal axis of the fixation helix.

20 Claims, 10 Drawing Sheets

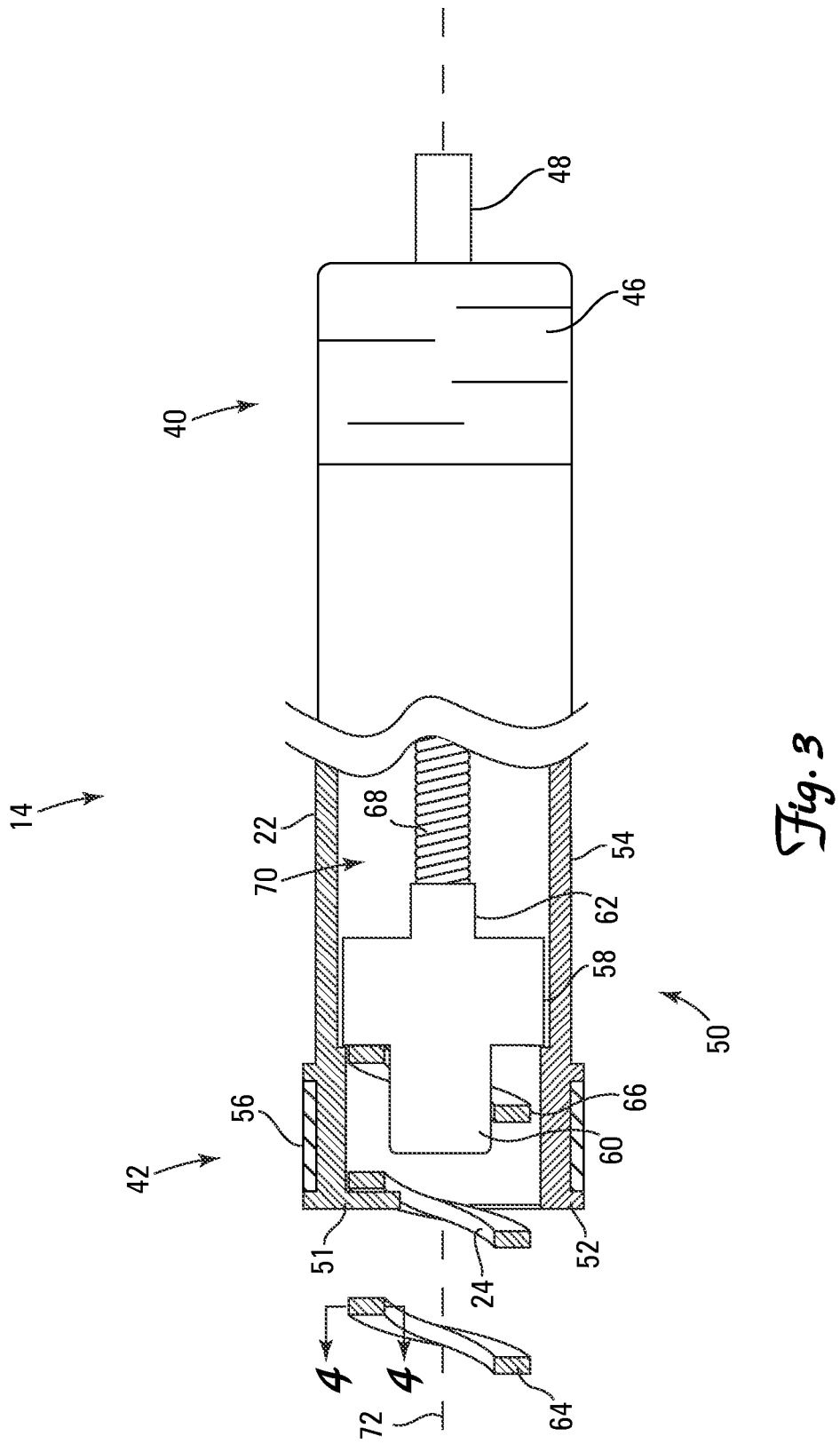

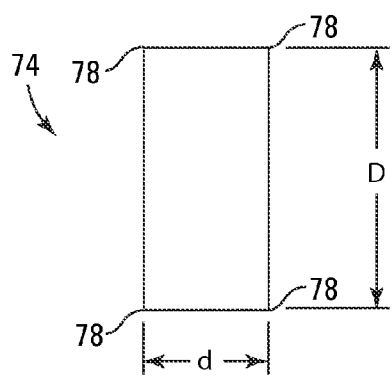
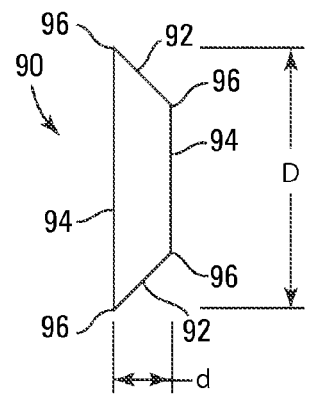
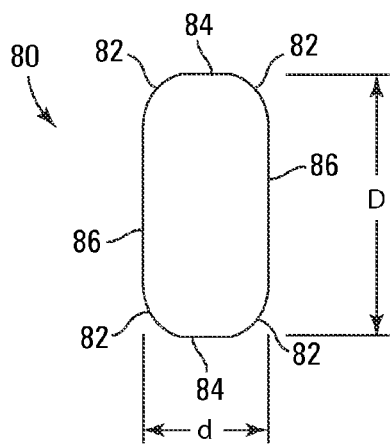
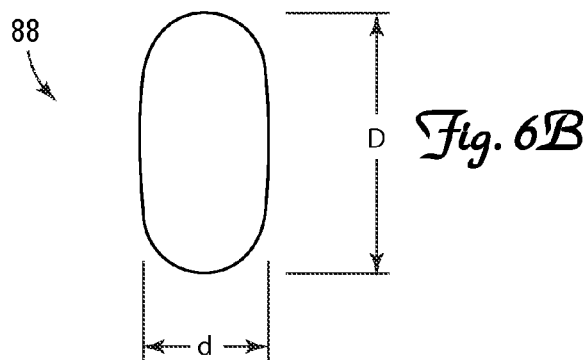

HELIX FIXATION MECHANISM

CROSS-REFERENCES TO RELATED APPLICATIONS

This application claims the benefit under 35 U.S.C. §119 (e) to U.S. Provisional Patent Application No. 61/260,583, filed on Nov. 12, 2009, entitled "HELIX FIXATION MECHANISM," which is incorporated herein by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Various implantable leads including a fixation helix formed of a filar having a non-circular cross-sectional profile are disclosed herein. In various examples, the filar of the fixation helix has a major dimension and a minor dimension, the major dimension being disposed transversely to a longitudinal axis of the helical electrode.

In example 1, an implantable lead has a flexible body extending between a proximal end and a distal end. A connector assembly is secured to the proximal end for coupling the lead to an implantable medical device while a distal assembly is coupled to the distal end. The connector assembly includes a terminal pin that is rotatable relative to the body. A conductor member is rotatably disposed longitudinally within the body and is coupled to the terminal pin. The distal assembly includes a housing having a distal region and a proximal region. The proximal region is fixedly coupled to the distal end of the body. A coupler having a proximal region and a distal region is rotatably disposed within the housing. A helical electrode is secured to the coupler and extends distally therefrom. The helical electrode is formed of a filar having a non-circular cross-sectional profile with a major dimension and a minor dimension less than the major dimension. The major dimension is disposed transversely to a longitudinal axis of the helical electrode. The terminal pin is rotatably engaged with the coupler via the conductor member such that rotation of the terminal pin causes the coupler and the helical electrode to rotate and therefore translate relative to the housing.

In Example 2, the implantable lead of Example 1, wherein the major dimension is disposed at an angle of about 30 to about 90 degrees with respect to the longitudinal axis of the helical electrode.

In Example 3, the implantable lead of Example 1 or Example 2, wherein the major dimension of the filar is at least about twice the minor dimension.

In Example 4, the implantable lead of any of Examples 1-3, wherein the filar has a cross-sectional profile having rounded corners.

In Example 5, the implantable lead of any of Examples 1-3, wherein the filar has a cross-sectional profile having square corners.

In Example 6, the implantable lead of any of Examples 1-5, wherein the helical electrode is resilient and collapsible so that it has a first maximum outer diameter when inside the housing and a second maximum outer diameter when extended out of the housing, the second maximum outer diameter being different than the first maximum outer diameter.

In Example 7, the implantable lead of any of Examples 1-6, wherein the helical electrode is resilient and collapsible so that at least a portion of the helix has a first pitch when inside the housing and a second pitch when extended out of the housing, the second pitch being different than the first pitch.

In Example 8, the implantable lead of any of Examples 1-3 and 6-7, wherein the filar has one of a hemispherical cross-sectional profile, an elliptical cross-sectional profile, or a polygonal cross-sectional profile.

In Example 9, the implantable lead of any of Examples 1-8, wherein the filar is a composite filar having an outer sleeve and an inner core disposed within the outer sleeve, the outer sleeve and the inner core formed of different materials.

In Example 10, the implantable lead of any of Examples 1-9, wherein at least a portion of the helical electrode includes a surface treatment to improve a tissue holding property of the helical electrode.

In Example 11, an implantable lead is configured to carry an electrical signal and deliver a therapeutic electrical stimulus to cardiac tissue in a patient, and includes a flexible body extending between a proximal end and a distal end. An electrical conductor extends within the flexible body to carry an electrical signal therethrough. A distal assembly is coupled to the distal end of the body. The distal assembly includes a housing having a proximal region that is fixedly coupled to the distal end of the body and a distal region that includes a distal end. A coupler having a proximal region and a distal region is rotatably disposed within the housing. A fixation helix is attached to the coupler and extends distally therefrom. The fixation helix is formed of a filar having a non-circular cross-sectional profile having a major dimension and a minor dimension, the major dimension disposed transversely to a longitudinal axis of the fixation helix.

In Example 12, the implantable lead of Example 11, wherein the major dimension is disposed at an angle of about 30 to about 90 degrees with respect to the longitudinal axis of the fixation helix.

In Example 13, the implantable lead of Example 11 or Example 12, wherein at least a portion of the helical electrode has an outer diameter that varies along a length of the fixation helix when extending distally from the housing.

In Example 14, the implantable lead of any of Examples 11-13, wherein at least a portion of the fixation helix has a pitch that varies along a length of the fixation helix when extending distally from the housing.

In Example 15, the implantable lead of any of Examples 11-14, wherein the filar has one of a hemispherical cross-sectional profile, an elliptical cross-sectional profile, or a polygonal cross-sectional profile.

In Example 16, the implantable lead of any of Examples 11-15, wherein the fixation helix is formed from a composite filar having an outer sleeve and an inner core disposed within the outer sleeve, the outer sleeve and the inner core formed of different materials.

In Example 17, the implantable lead of any of Examples 11-16, wherein at least a portion of the fixation helix includes a surface treatment.

In Example 18, an implantable lead is configured to carry an electrical signal and includes a flexible body extending between a proximal end and a distal end. An electrical conductor extends within the flexible body to carry an electrical signal therethrough. A distal assembly is coupled to the distal end of the body. The distal assembly includes a housing having a proximal region that is fixedly coupled to the distal end of the body and a distal region that includes a distal end. A coupler having a proximal region and a distal region is rotatably disposed within the housing. A fixation helix is attached to the coupler and extends distally from the coupler. The fixation helix has a retracted configuration and an extended configuration, wherein one or both of a pitch and an outer maximum diameter of at least a portion of the fixation helix varies along the length thereof when the helix is in the extended configuration.

In Example 19, the implantable lead of Example 18, wherein at least a portion of the fixation helix has a non-uniform pitch when in the extended configuration.

In Example 20, the implantable lead of Example 18 or Example 19, wherein at least a portion of the fixation helix has a non-uniform outer diameter when in the extended configuration.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 3 is a longitudinal cross-sectional view of the lead of FIG. 1.

FIG. 4 is a cross-section of a portion of the lead of FIG. 1.

FIGS. 6A-6C are schematic cross-sectional views of filars.

Figure 1:
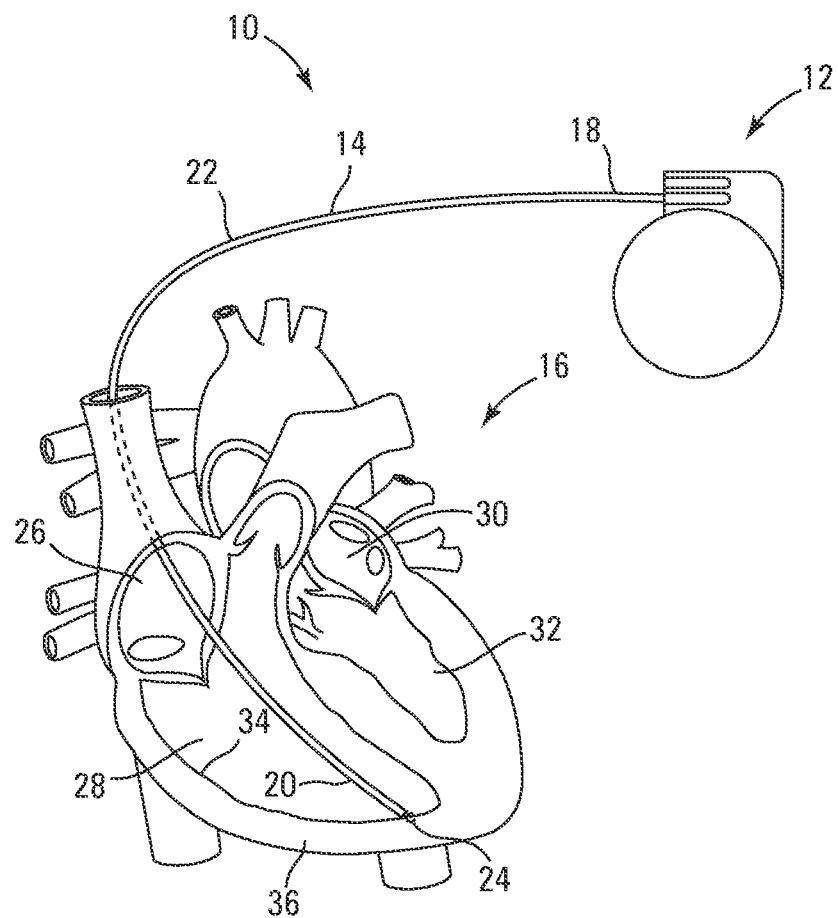
FIG. 1 is a combined cutaway and perspective view of an implantable medical device and lead in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable cardiac rhythm management (CRM) system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes a fixation helix 24, which, as will be discussed in greater detail below, locates and/or secures the distal region 20 within the heart 16. As will be explained in detail below, the distal region 20 of the lead 14 includes configurations of the fixation helix 24 that provide improved tissue holding performance.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities, e.g., a CRT-D device.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus operates as a helical electrode for sensing the electrical activity of the heart 16 and/or applying a stimulating pulse to the right ventricle 28. In other embodiments, the fixation helix 24 is not electrically active. Rather, in some embodiments, other components of the lead 14 are electrically active.

Figure 2:
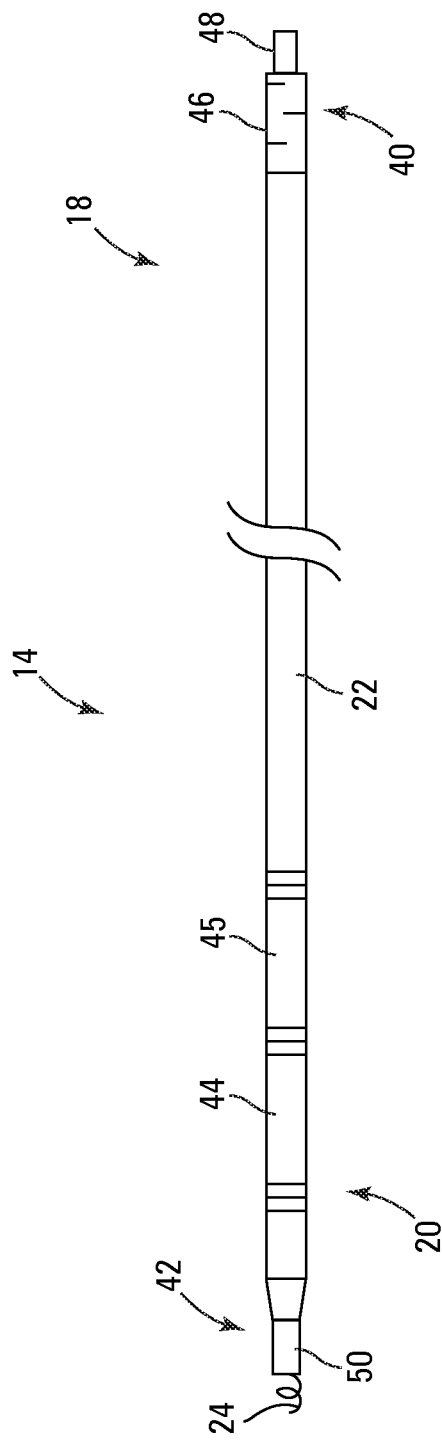
FIG. 2 is a side elevation view of the lead of FIG. 1.

FIG. 2 is an isometric illustration of the lead 14. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 may include one or more electrodes. In the illustrated embodiment, the distal region 20 includes a pair of coil electrodes 44 and 45 that can function as shocking electrodes for providing a defibrillation shock to the heart 16. In some embodiments, one or more of the coil electrodes 44 and 45 may act as low voltage pace or sense electrodes.

In various embodiments, the lead 14 may include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations may be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1). In various embodiments, the terminal pin 48 extends proximally from the connector 46 and in some embodiments is coupled to a conductor member (not visible in this view) that extends longitudinally through the lead body 22 such that rotating the terminal pin 48 (relative to the lead body 22) causes the conductor member to rotate within the lead body 22. In some embodiments, the terminal pin 48 includes an aperture extending therethrough in order to accommodate a guide wire or an insertion stylet. In some embodiments (not illustrated), the lead 14 may have a fixed helix 24 that can be secured into tissue by rotating the lead 14 itself, rather than by rotating any internal structure within the lead 14.

The distal assembly 42 includes a housing 50, within which the fixation helix 24 is at least partially disposed. In some embodiments, the housing 50 includes or accommodates a mechanism that enables the fixation helix 24 to move distally and proximally relative to the housing 50. In some embodiments, the housing 50 may accommodate or include structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a helical pace/sense electrode. In some embodiments, the fixation helix 24 is made of an electrically conductive material such as Elgiloy, MP35N, nickel, tungsten, tantalum, iridium, platinum, titanium, palladium, stainless steel as well as alloys of any of these materials. In some embodiments, the fixation helix 24 is made of a non-electrically conductive material such as PES (polyethersulfone), polyurethane-based thermoplastics, ceramics, polypropylene and PEEK (polyetheretherketone).

FIG. 3 is a cross-sectional view of the lead 14. As shown in FIG. 3, the housing 50 includes a distal region 52 and a proximal region 54. The housing 50 is, in general, relatively rigid or semi-rigid. In some embodiments, the housing 50 is made of an electrically conductive material such as Elgiloy, MP35N, nickel, tungsten, tantalum, iridium, platinum, titanium, palladium, stainless steel as well as alloys of any of these materials. In some embodiments, the housing 50 is made of a non-electrically conductive material such as PES, polyurethane-based thermoplastics, ceramics, polypropylene and PEEK.

In the illustrated embodiment, a drug eluting collar 56 is disposed about an exterior of the housing 50 within the distal region 52. In various embodiments, the drug eluting collar 56 is configured to provide a time-released dosage of a steroid or other anti-inflammatory agent to the tissue to be stimulated, e.g., the heart tissue in which the electrically active fixation helix 24 is implanted. While not illustrated, in some embodiments the distal assembly 42 may include a radiopaque element disposed under the drug eluting collar 56.

The distal assembly 42 includes a coupler 58 that has a distal portion 60 and a proximal portion 62. In some embodiments, the coupler 58 is formed of a metallic material and is configured to move longitudinally and/or rotationally with respect to the housing 50. In some embodiments, as illustrated, the distal portion 60 may have a relatively smaller diameter (relative to the proximal portion 62) in order to accommodate the fixation helix 24. While not illustrated, in some embodiments the proximal portion 62 is configured to accommodate a seal that provides a seal between the coupler 58 and the housing 50.

The fixation helix 24 has a distal region 64 and a proximal region 66. The proximal region 66 of the fixation helix 24 is secured to the distal portion 60 of the coupler 58 using any suitable attachment technique. In some embodiments, the proximal region 66 of the fixation helix 24 is welded or soldered onto the distal portion 60 of the coupler 58. In some embodiments, the proximal region 66 of the fixation helix 24 has an inner diameter that is less than an outer diameter of the distal portion 60 of the coupler 58, and thus is held in place via compressive forces. In some embodiments the fixation helix 24 is adhesively secured to the distal portion 60 of the coupler 58. In some embodiments, multiple attachment techniques are used to secure the fixation helix 24 to the coupler 58.

As further shown, the lead 14 includes a conductor member 68 disposed within the lead body 22. The conductor member 68 has a proximal region (not visible) and a distal region 70. As shown, the distal region 70 is secured to the proximal portion 62 of the coupler 58, and the conductor member 68 extends proximally through the lead body 22 to the connector assembly 40. The proximal region of the conductor member 68 is coupled to the terminal pin 48 such that rotation of the terminal pin 48 causes the conductor member 68, and consequently, the coupler 58, to rotate.

As discussed herein, the lead 14 is an extendable/retractable lead. Thus, the housing 50 includes structure to convert rotational movement of the coupler 58 (and hence the fixation helix 24) relative to the housing 50 into translational movement of the coupler 58 (and hence the fixation helix 24) relative to the housing 50. In the illustrated embodiment, the housing 50 includes a peg 51 that the fixation helix 24 can rotate against and hence translate relative to the housing 50.

In other embodiments, any arrangement, whether now known or later developed, for providing the extendable/retractable functionality of the fixation helix 24 can be utilized in connection with the various embodiments of the present invention. In one embodiment, the lead 14 includes structures such as those described and illustrated in co-pending and commonly assigned U.S. Provisional Patent Application 61/181,954, the disclosure of which is incorporated by reference herein in its entirety. In other embodiments, a different arrangement for extending and retracting the fixation helix 24 is utilized.

The lead 14 can be considered as having a longitudinal axis 72. As will be explained below, in various embodiments, the fixation helix 24 is configured to exhibit performance advantages compared to conventional fixation helix designs. These advantages include, for example, increased tissue holding capability at relatively small helix diameters. As a result, the fixation helix embodiments described herein advantageously provide for robust chronic fixation and resistance to spontaneous pull-out while still minimizing over-insertion. In some embodiments, smaller surface areas may contribute to improved electrical performance.

FIG. 4 is a cross-section of the filar forming the fixation helix 24. As can be seen, the filar 74 has a major dimension D and a minor dimension d. In some embodiments, the major dimension D and the minor dimension d may be selected to provide desired tissue holding capability. For example, for a given filar cross-sectional area, increasing the major dimension D relative to the minor dimension d may increase holding power and resistance to inadvertent back-out.

In some embodiments, the major dimension D may be at least twice the minor dimension d. In some cases, the major dimension D and the minor dimension d may be related via a ratio of D:d of about 3:1, about 4:1, about 5:1, about 6:1, or greater, inclusive of intermediate ratios therebetween. In the illustrated embodiment, the filar 74 is configured such that the major dimension D is arranged transversely (i.e. not parallel to) the longitudinal axis 72.

Figure 5:
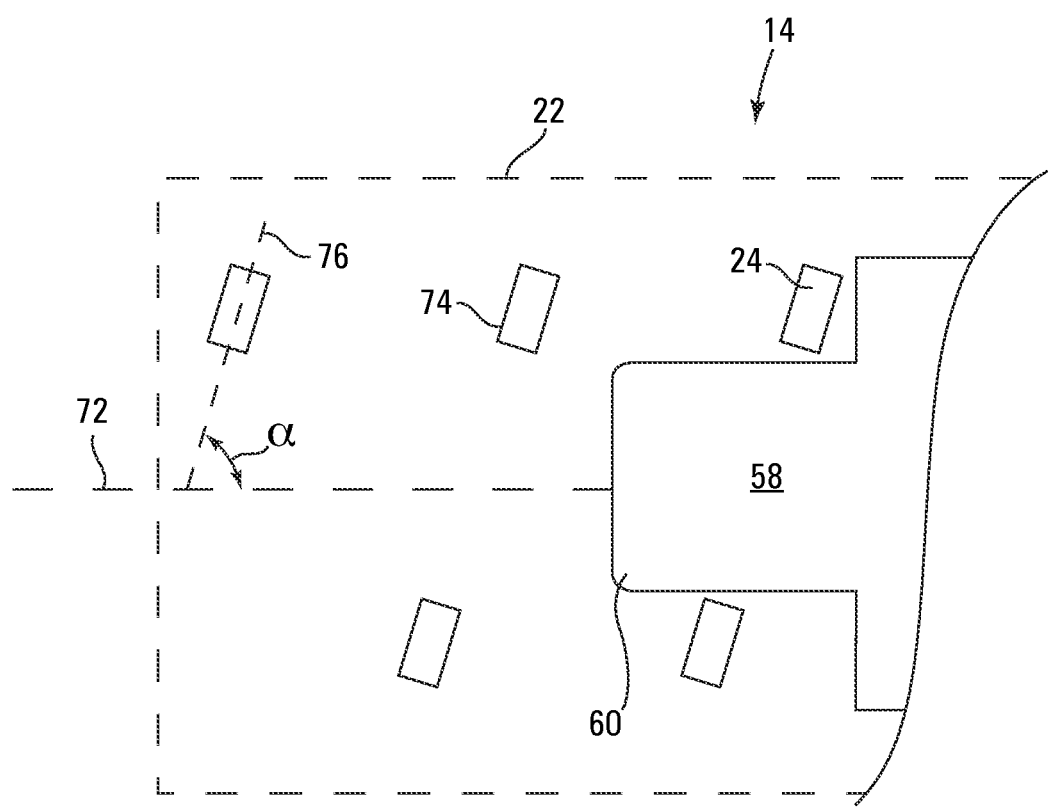
FIG. 5 is a longitudinal cross-sectional view of the lead of FIG. 1, showing the orientation of the filar with respect to a longitudinal axis of the lead of FIG. 1.

FIG. 5 is a schematic cross-section of the filar 74, showing its orientation with respect to the longitudinal axis 72 of the lead 14. In FIG. 5, an axis 76 can be considered as extending through the filar 74 along its major dimension, and the axis 76 forms an angle labeled a with the longitudinal axis 72 of the lead 14. In some embodiments, the angle α is selected to achieve desirable tissue holding properties. For example, in one embodiment, the angle α is approximately 90 degrees, and consequently, the major dimension, referenced by the axis 76, is oriented generally orthogonal to the longitudinal axis 72 of the lead 14. In this embodiment, the orientation of the filar 74 provides maximum tissue contact and thus provides maximum bearing surface resisting forces acting parallel to the longitudinal axis 72. As a result, the filar 74 resists both pull-out and over-insertion that can be caused by these forces.

In some embodiments, the filar 74 may be canted, or arranged at an angle of less than 90 degrees with respect to the longitudinal axis 72. In some cases, a may range from about 30 degrees to about 90 degrees. For example, in some embodiments, there may be a desire to make it easier for a physician to be able to remove the lead 14 by pulling on the lead 14 and thereby straightening the fixation helix 24. In such cases, it may be desirable to decrease the angle α.

Returning briefly to FIG. 4, it can be seen that the filar 74 is shown having a rectangular profile, i.e., the corners 78 are each square. In some embodiments, however, the filar 74 does not have a rectangular profile. FIGS. 6A-6C show illustrative but non-limiting examples of other suitable profiles for the filar.

FIG. 6A is a schematic cross-section of a filar 80 having rounded corners 82. As illustrated, the filar 80 has a pair of end surfaces 84 that are at least substantially parallel to each other. The filar 80 also has a pair of side surfaces 86 that are at least substantially parallel to each other. Even though the filar 80 is not rectangular in cross-sectional profile, the filar 80 is still considered as having a major dimension D and a minor dimension d that is perpendicular to the major dimension D, as shown.

FIG. 6B is a schematic cross-section of a filar 88 having an ovoid or elliptical cross-sectional profile. In the illustrated embodiment, the filar 88 has no or substantially no straight portions or sections. Nevertheless, the filar 88 may be considered as being defined by a major dimension D and a minor dimension d that is perpendicular to the major dimension D, as shown.

FIG. 6C is a schematic cross-section of a filar 90 having first and second end surfaces 92 and first and second side surfaces 94. As illustrated, the filar 90 has a trapezoidal cross-sectional profile in which the first end second side surfaces 94 are parallel to each other while the first and second end surfaces 92 are not. In some embodiments, the filar 90 may have a parallelogram cross-sectional profile in which the first and second end surfaces 92 are parallel to each other.

In some embodiments, the filar 90 may have a cross-sectional profile defined by any one of a variety of different polygons. As illustrated, the filar 90 has corners 96. In some embodiments, one or more of the corners 96 may be rounded. As shown, the filar 90 may be considered as being defined by a major dimension D and a minor dimension d that is perpendicular to the major dimension D.

Figure 7:
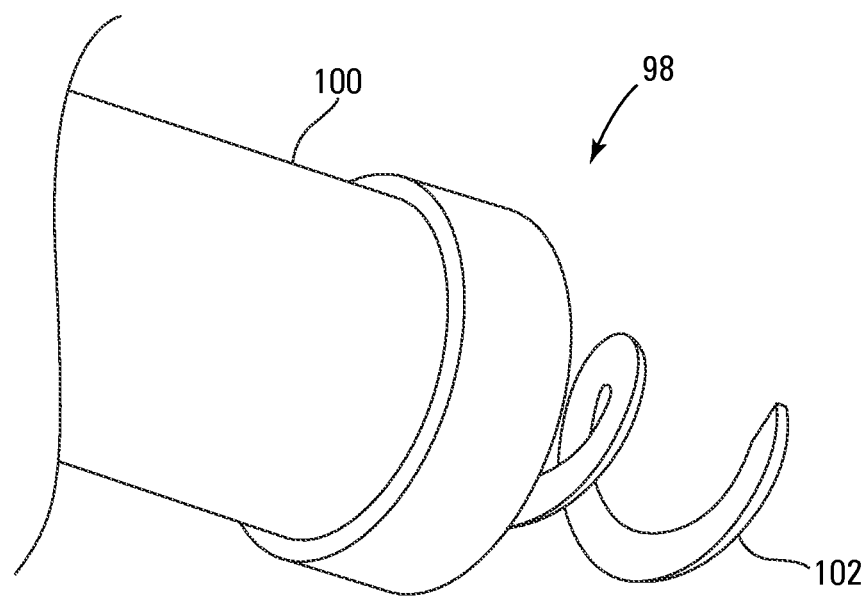
FIG. 7 is a perspective view of a distal portion of a lead.

FIG. 7 is a perspective view of a distal portion of a lead 98 according to another embodiment of the present invention. The lead 98 includes a distal housing 100 that may be similar to the housing 50 described with respect to the lead 14. A fixation helix 102 is shown in an extended position, extending distally from the distal housing 100. The fixation helix 102 may be considered as having a flattened, elliptical or semi-elliptical shape.

Figure 8:
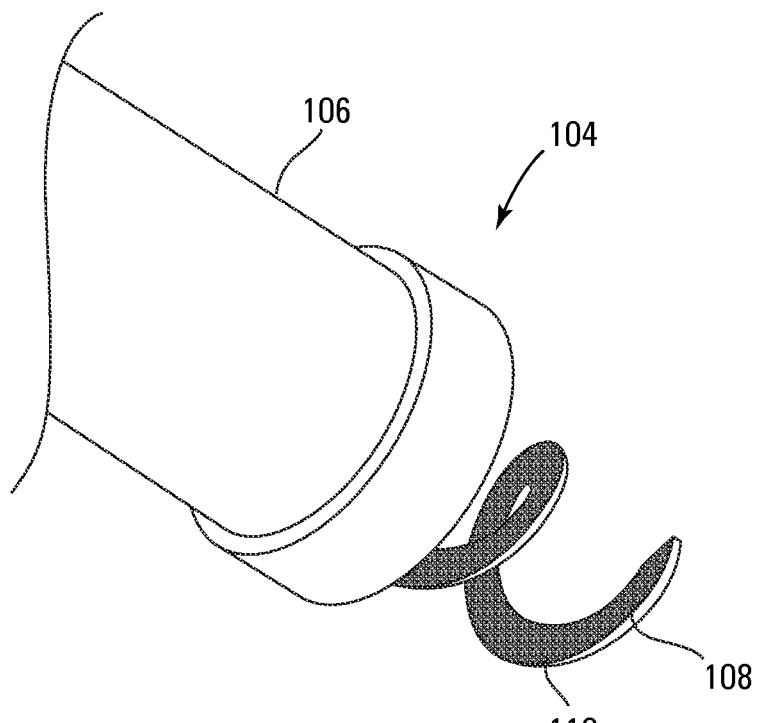
FIG. 8 is a perspective view of a distal portion of a lead.

FIG. 8 is a perspective view of a distal portion of a lead 104 according to another embodiment of the present invention. The lead 104 includes a distal housing 106 that may be similar to the housing 50 described with respect to the lead 14. A fixation helix 108 having a cross-sectional profile similar to the fixation lead 102 (FIG. 7) is shown in an extended position, extending distally from the distal housing 106. In the illustrated embodiment, the fixation helix 108 includes a surface treatment 110 formed or deposited on at least part of the fixation helix 108. In some embodiments, the surface treatment 110 may improve tissue holding, reduce inadvertent back-out, or other desirable properties.

In some embodiments, the surface treatment 110 represents a material that is chemically or physically applied to the fixation helix 108. Illustrative but non-limiting examples of suitable coatings include coatings that are known to encourage tissue in-growth, such as ePTFE (expanded polytetrafluoroethylene). Other suitable coatings include iridium oxide, platinum black, or a powdered metal including small spheres or rods of the base electrode material that can be sintered or sputtered into place.

In some cases, the surface treatment 110 represents the removal of material from the fixation helix 108. This can be accomplished, for example, via a variety of techniques such as, but not limited to, etching, sand blasting and the like. In some cases, the surface treatment 110 may represent a random roughening of the surface of the fixation helix 108. In some cases, the surface treatment 110 may represent an ordered pattern such as parallel lines, raised pyramidal shapes, and the like.

Figure 9:
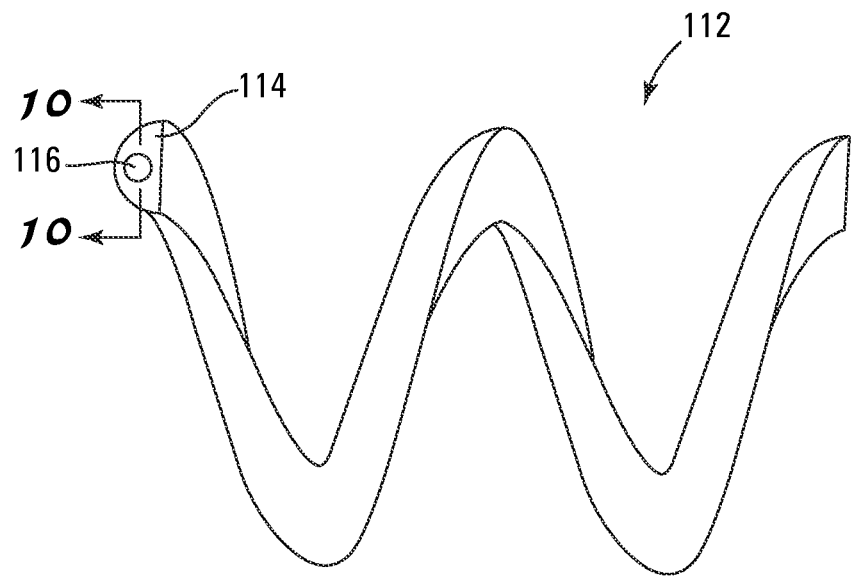
FIG. 9 is a perspective view of a portion of a fixation helix.

FIG. 9 is a schematic view of a filar 112 that may be used to form a fixation helix such as the fixation helix 24 discussed above. The filar 112 has an outer sleeve 114 that surrounds an inner core 116. In some cases, the inner core 116 may be formed of a different material from the outer sleeve 114, and thus may alter the physical properties of the filar 112. For example, the inner core 116 may be formed of a material that is stronger than the outer sleeve 114, and therefore may improve resistance to straightening.

In some embodiments, one or more of the outer sleeve 114 and the inner core 116 may independently be formed of metallic or polymeric materials. Examples of metallic materials include but are not limited to Elgiloy, MP35N, tungsten, tantalum, iridium, platinum, titanium, palladium, stainless steel, as well as alloys of any of these materials. Examples of polymeric materials include but are not limited to PES (polyethersulfone), polyurethane-based thermoplastics, ceramics, polypropylene and PEEK (polyetheretherketone).

In some embodiments, the outer sleeve 114 may be formed of a relatively soft metal like platinum, palladium or alloys thereof while the inner core 116 may be formed of a relatively stiffer metal such as Elgiloy, PP35N or stainless steel or even a stiff polymer such as PES (polyethersulfone). In some embodiments, the outer sleeve 114 may be formed of a polymeric material while the inner core 116 may be formed of a relatively stiffer metal such as Elgiloy, PP35N or stainless steel or even a stiff polymer such as PES (polyethersulfone).

Figure 10:
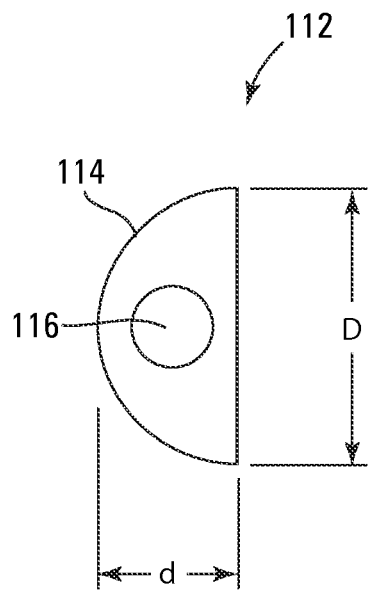
FIG. 10 is a cross-sectional view taken along line 10-10 of FIG. 9.

FIG. 10 is a cross-sectional view of the fixation helix 112. In the illustrated embodiment, the fixation helix 112 has a semicircular cross-sectional profile. Even though the fixation helix 112 is not rectangular in cross-sectional profile, the fixation helix 112 is still considered as having, in cross-section, a major dimension D and a minor dimension d that is perpendicular to the major dimension D, as shown.

In some embodiments, a composite helix such as the fixation helix 112 may take on other cross-sectional profiles such as those discussed above. Moreover, in some embodiments, a composite helix such as the fixation helix 112 may include a surface treatment such as the surface treatment 110 described above. In some embodiments, a fixation helix may include several of the features described herein, as shown in FIG. 11.

Figure 11:
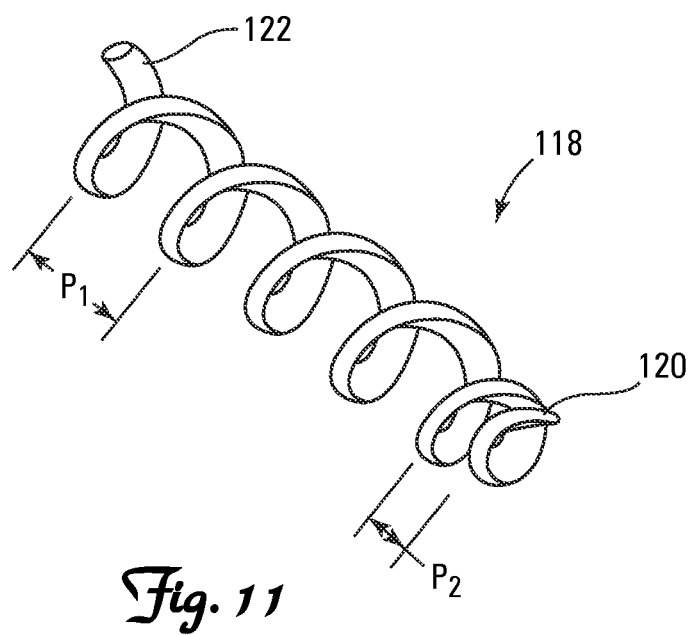
FIG. 11 is a perspective view of a portion of a fixation helix.

FIG. 11 is a perspective view of a portion of a fixation helix 118 that has a distal region 120 and a proximal region 122. Fixation helix 118 combines several features. As can be seen, the fixation helix 118 has an outer diameter that is larger near the proximal region 122 and decreases in proximity to the distal region 120. In the illustrated embodiment, the fixation helix 118 has a pitch, or distance between adjacent turnings, that decreases with proximity to the distal region 120. In this, pitch is defined as the distance between a mid-point of a first turning and a mid-point of an adjacent turning. Near the proximal region 122, the fixation helix 118 has a pitch labeled as $P_1$. Near the distal region 120, the fixation helix 118 has a pitch labeled $P_2$, which is smaller than the pitch $P_1$.

In some embodiments, the non-uniform outer diameter and/or non-uniform pitch may improve tissue holding, particularly once the tissue heals from initial penetration of the fixation helix 118. In some embodiments, the fixation helix 118 may have a semicircular cross-sectional profile (similar to that shown in FIG. 10) and/or a surface treatment on at least a portion of the fixation helix 118.

Figure 12A:
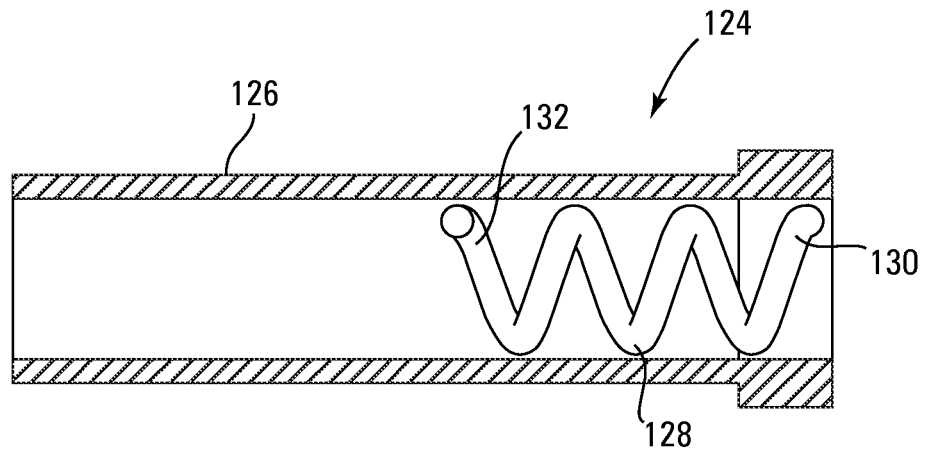
FIGS. 12A-12B are schematic views of a distal portion of a lead.
Figure 12B:
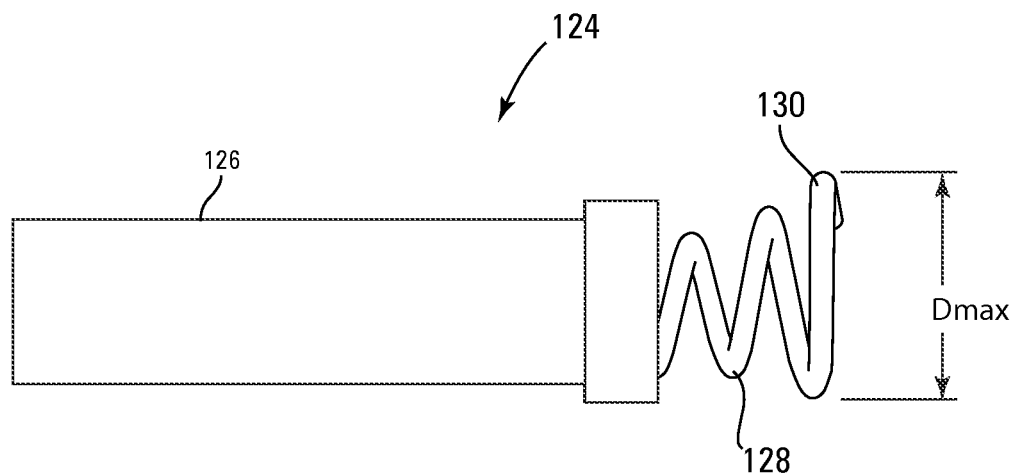

FIGS. 12A and 12B provide a schematic view of another embodiment of the present invention in which a fixation helix is formed of a material that permits the fixation helix to change its shape or configuration in moving from a retracted position in which the fixation helix remains within a housing to an extended position in which at least a portion of the fixation helix extends distally from the housing. In some embodiments, the fixation helix may be formed of a material that is sufficiently resilient such that the fixation helix can be compressed from a relaxed configuration for placement within a lead housing. In some embodiments, the fixation helix may be made of a shape memory material such as a shape memory polymer or a shape memory metal. In some embodiments, the fixation helix may be made of a nickel-titanium alloy such as Nitinol.

FIG. 12A shows a distal portion of a lead 124 in which a fixation helix 128 is retracted within a housing 126. The fixation helix 128 has a distal end 130 and a proximal end 132. In the retracted position, the fixation helix 128 has a uniform outer diameter and pitch in order to fit within the housing 126. While the fixation helix 128 is generically shown as having a circular cross-sectional profile, in some embodiments the fixation helix 128 may have a non-circular cross-sectional profile such as those discussed above.

In FIG. 12B, the outer diameter of the fixation helix 128 increases as the fixation helix 128 exits the housing 126. As shown, the fixation helix 128 has a maximum outer diameter labeled $D_{max}$ at or near the distal end 130 of the fixation helix 128. In some embodiments, the fixation helix 128 may have an outer diameter (when deployed) that is substantially constant (but greater than its retracted diameter). In some embodiments, the fixation helix 128 may have an outer diameter (when deployed) that is greatest at the distal end 130 and that decreases moving proximally therefrom.

Figure 13:
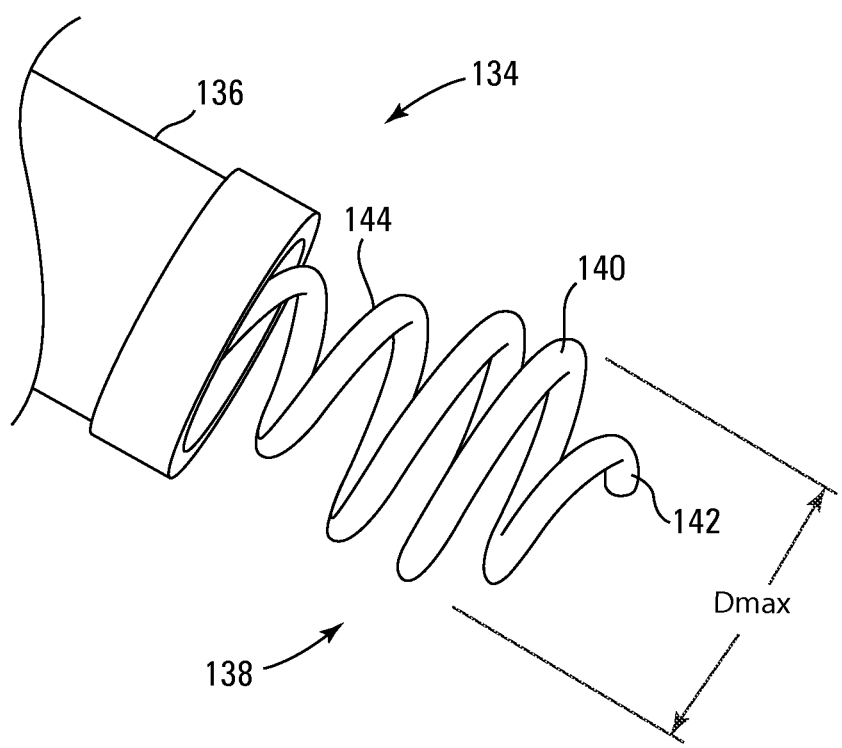
FIG. 13 is a perspective view of a distal portion of a lead.

FIG. 13 is a schematic view of a distal portion of a lead 134 that includes a housing 136 and a fixation helix 138 extending distally from the housing 136. In this embodiment, the fixation helix 138 has a maximum outer diameter labeled $D_{max}$ at a point 140. From the point 140, the outer diameter can be seen as decreasing in the distal direction, towards a distal end 142, as well as decreasing in a proximal direction, towards a proximal region 144.

The leads described herein, such as the lead 14, the lead 98, the lead 104, the lead 124 and the lead 134, as well as leads that incorporate fixation helixes such as the fixation helix 112 and the fixation helix 118, include features that enhance desirable properties such as tissue holding and resistance to inadvertent back-out.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead comprising:
    a flexible body extending between a proximal end and a distal end;
    a connector assembly secured to the proximal end for coupling the lead to an implantable medical device, the connector assembly including a terminal pin rotatable relative to the body;
    a conductor member disposed longitudinally within the body and coupled to the terminal pin, the conductor member rotatable relative to the body; and
    a distal assembly coupled to the distal end of the body and including:
        a housing having a distal region and a proximal region, the proximal region fixedly coupled to the distal end of the body;
        a coupler rotatably disposed within the housing, the coupler having a proximal region and a distal region, the proximal region connected to the conductor member; and
        a helical electrode secured to the coupler and extending distally therefrom, the helical electrode formed of a filar canted at an angle of less than 90 degrees with respect to a longitudinal axis of the helical electrode, the filar having a non-circular cross-sectional profile with outer side surfaces that are at least substantially parallel to each other, the filar having a major dimension and a minor dimension less than the major dimension, the major dimension disposed transversely to the longitudinal axis; and
        wherein the terminal pin is rotatably engaged with the coupler via the conductor member such that rotation of the terminal pin causes the coupler and the helical electrode to rotate and therefore translate relative to the housing.

2. The implantable lead of claim 1, wherein the major dimension is disposed at an angle of at least about 30 degrees with respect to the longitudinal axis of the helical electrode.

3. The implantable lead of claim 1, wherein the major dimension of the filar is at least about twice the minor dimension.

4. The implantable lead of claim 1, wherein the filar has a cross-sectional profile having rounded corners.

5. The implantable lead of claim 1, wherein the filar has a cross-sectional profile having square corners.

6. The implantable lead of claim 1, wherein the helical electrode is resilient and collapsible so that it has a first maximum outer diameter when inside the housing and a second maximum outer diameter when extended out of the housing, the second maximum outer diameter being different than the first maximum outer diameter.

7. The implantable lead of claim 1, wherein the helical electrode is resilient and collapsible so that at least a portion of the helix has a first pitch when inside the housing and a second pitch when extended out of the housing, the second pitch being different than the first pitch.

8. The implantable lead of claim 1, wherein the filar has one of a hemispherical cross-sectional profile, an elliptical cross-sectional profile, or a polygonal cross-sectional profile.

9. The implantable lead of claim 1, wherein the filar is a composite filar having an outer sleeve and an inner core disposed within the outer sleeve, the outer sleeve and the inner core formed of different materials.

10. The implantable lead of claim 1, wherein at least a portion of the helical electrode includes a surface treatment to improve a tissue holding property of the helical electrode.

11. An implantable lead configured to carry an electrical signal and deliver a therapeutic electrical stimulus to cardiac tissue in a patient, the implantable lead comprising:
a flexible body extending between a proximal end and a distal end;
an electrical conductor extending within the body to carry an electrical signal through the body; and
a distal assembly coupled to the distal end of the body and including:
a housing having a distal region and a proximal region, the proximal region fixedly coupled to the distal end of the body, the distal region including a distal end;
a coupler rotatably disposed within the housing, the coupler having a proximal region and a distal region; and
a fixation helix attached to the coupler and extending distally therefrom;
wherein the fixation helix is formed of a filar canted at an angle of less than 90 degrees with respect to a longitudinal axis of the helical electrode, the filar having a non-circular cross-sectional profile with outer side surfaces that are at least substantially parallel to each other, the filar having a major dimension and a minor dimension, the major dimension disposed transversely to a longitudinal axis of the fixation helix.

12. The implantable lead of claim 11, wherein the major dimension is disposed at an angle of at least about 30 degrees with respect to the longitudinal axis of the fixation helix.

13. The implantable lead of claim 11, wherein at least a portion of the helical electrode has an outer diameter that varies along a length of the fixation helix when extending distally from the housing.

14. The implantable lead of claim 11, wherein at least a portion of the fixation helix has a pitch that varies along a length of the fixation helix when extending distally from the housing.

15. The implantable lead of claim 11, wherein the filar has one of a hemispherical cross-sectional profile, an elliptical cross-sectional profile, or a polygonal cross-sectional profile.

16. The implantable lead of claim 11, wherein the fixation helix is formed from a composite filar having an outer sleeve and an inner core disposed within the outer sleeve, the outer sleeve and the inner core formed of different materials.

17. The implantable lead of claim 11, wherein at least a portion of the fixation helix includes a surface treatment.

18. An implantable lead configured to carry an electrical signal, the implantable lead comprising:
a flexible body extending between a proximal end and a distal end;
an electrical conductor extending within the body to carry an electrical signal from the proximal end to the distal end; and
a distal assembly coupled to the distal end of the body and including:
a housing having a distal region and a proximal region, the proximal region fixedly coupled to the distal end of the body, the distal region including a distal end;
a coupler rotatably disposed within the housing, the coupler having a proximal region and a distal region; and
a fixation helix attached to the coupler and extending distally therefrom;
wherein the fixation helix is formed of a filar canted at an angle of less than 90 degrees with respect to a longitudinal axis of the helical electrode and has a retracted configuration and an extended configuration, the filar having a non-circular cross-sectional profile with outer side surfaces that are at least substantially parallel to each other, wherein one or both of a pitch and an outer maximum diameter of at least a portion of the fixation helix varies along the length thereof when the helix is in the extended configuration.

19. The implantable lead of claim 18, wherein at least a portion of the fixation helix has a non-uniform pitch when in the extended configuration.

20. The implantable lead of claim 18, wherein at least a portion of the fixation helix has a non-uniform outer diameter when in the extended configuration.

* * * * *